United States Patent
Fugazza et al.

(10) Patent No.: US 10,483,008 B2
(45) Date of Patent: Nov. 19, 2019

(54) PROCESS FOR THE PURIFICATION OF GA-68 FROM ELUATE DERIVING FROM $^{68}$GE/$^{68}$GA GENERATORS AND CHROMATOGRAPHIC COLUMNS FOR USE IN SAID PROCESS

(71) Applicant: ADVANCED ACCELERATOR APPLICATIONS INTERNATIONAL S.A., Geneva (CH)

(72) Inventors: Lorenza Fugazza, Ivrea (IT); Maurizio Franco Mariani, Ivrea (IT)

(73) Assignee: Advanced Accelarator Applications International S.A., Geneva (CH)

( * ) Notice: Subject to any disclaimer, the term of this patent is extended or adjusted under 35 U.S.C. 154(b) by 240 days.

(21) Appl. No.: 15/545,510

(22) PCT Filed: Jan. 28, 2016

(86) PCT No.: PCT/EP2016/051764
§ 371 (c)(1),
(2) Date: Jul. 21, 2017

(87) PCT Pub. No.: WO2016/120365
PCT Pub. Date: Aug. 4, 2016

(65) Prior Publication Data
US 2018/0005719 A1    Jan. 4, 2018

(30) Foreign Application Priority Data

Jan. 30, 2015   (IT) .................................. FI2015A0018

(51) Int. Cl.
| | |
|---|---|
| *B01D 15/08* | (2006.01) |
| *B01D 15/36* | (2006.01) |
| *B01J 20/10* | (2006.01) |
| *B01J 20/28* | (2006.01) |
| *B01J 20/283* | (2006.01) |
| *B01J 41/20* | (2006.01) |
| *C07B 59/00* | (2006.01) |
| *C22B 3/42* | (2006.01) |
| *C22B 58/00* | (2006.01) |
| *G21F 9/12* | (2006.01) |
| *G21G 1/00* | (2006.01) |
| *A61K 51/08* | (2006.01) |

(52) U.S. Cl.
CPC .............. *G21F 9/12* (2013.01); *B01D 15/363* (2013.01); *B01J 20/103* (2013.01); *B01J 20/283* (2013.01); *B01J 20/28004* (2013.01); *B01J 41/20* (2013.01); *C07B 59/008* (2013.01); *C22B 3/42* (2013.01); *C22B 58/00* (2013.01); *A61K 51/08* (2013.01)

(58) Field of Classification Search
CPC ............ G21F 9/12; B01D 15/08; B01D 15/10; B01D 15/325; B01D 15/362; B01D 15/363; B01J 20/103; B01J 20/28004; B01J 20/283; B01J 41/20; C22B 3/42; C22B 58/00; G21G 1/0005; G21G 1/001; G21G 1/04; G21G 2001/0021; G21G 4/08; A61K 51/048; A61K 51/083; A61K 51/088; A61K 51/1282; A61K 51/0482; A61K 2123/00; A61K 51/08; G21H 5/02; C07B 59/00; C07B 59/008; C07F 7/081; C07F 7/30

See application file for complete search history.

(56) References Cited

U.S. PATENT DOCUMENTS

| | | | | |
|---|---|---|---|---|
| 4,264,468 | A  * | 4/1981 | Neirinckx | .......... A61K 51/1282 |
| | | | | 250/432 PD |
| 2008/0035542 | A1 | 2/2008 | Mourtada et al. | |
| 2009/0001283 | A1 | 1/2009 | Fitzsimmons et al. | |
| 2010/0202915 | A1* | 8/2010 | Zhernosekov | ............ G21H 5/02 |
| | | | | 420/1 |
| 2014/0171637 | A1* | 6/2014 | Fugazza | ............... A61K 51/088 |
| | | | | 540/465 |
| 2015/0098895 | A1* | 4/2015 | Mueller | ............... A61K 51/048 |
| | | | | 424/1.11 |

FOREIGN PATENT DOCUMENTS

| | | |
|---|---|---|
| DE | 102012208377 A1 | 11/2013 |
| WO | 2004089517 A1 | 10/2004 |
| WO | 2006056395 A2 | 6/2006 |
| WO | 2010114308 A1 | 10/2010 |
| WO | 2011033120 A2 | 3/2011 |

OTHER PUBLICATIONS

International Search Report for PCT/EP2016/051764 dated May 23, 2016.
Caletka, et al., "Separation of Germanium from Some Elements by Adsorption on Silica Gel," Journal of Radioanalytical Chemistry, vol. 21, 349-353 (1974).
Zhernosekov, et al., "Processing of Generator-Produced 68Ga for Medical Application," The Journal of Nuclear Medicine, vol. 48, No. 10, 1741-1748 (2007).
Notification of Transmittal of the International Preliminary Report on Patentability dated Apr. 20, 2017.

* cited by examiner

*Primary Examiner* — Benjamin L Lebron
(74) *Attorney, Agent, or Firm* — Abelman, Frayne & Schwab

(57) ABSTRACT

Chromatography columns for the purification of eluates from $^{68}$Ge/$^{68}$Ga generators comprising silica as stationary phase and purification processes that use said columns are described.

2 Claims, No Drawings

PROCESS FOR THE PURIFICATION OF GA-68 FROM ELUATE DERIVING FROM $^{68}$GE/$^{68}$GA GENERATORS AND CHROMATOGRAPHIC COLUMNS FOR USE IN SAID PROCESS

RELATED APPLICATIONS

This application is a national phase of International Application No. PCT/EP2016/051764 filed Jan. 28, 2016, and claims priority from Italian Patent Application No. FI2015A000018 filed Jan. 30, 2015, both incorporated by reference in their entirety.

FIELD OF THE INVENTION

The present invention relates to the purification processes of radioactive isotopes, in particular the purification of eluates containing Ga-68 deriving from $^{68}$Ge/$^{68}$Ga generators.

PRIOR ART

As is known, radioactive isotopes are widely used in medicine both for diagnostic purposes and for therapeutic purposes; in particular, radioactive isotopes of a metallic nature are bonded, by means of appropriate chelating agents, to carrier molecules (such as peptides) capable of recognizing and interacting (both in vivo and in vitro) with specific cell receptors so as to allow the detection and/or the destruction of diseased cells.

This labeling strategy is well suited to the production of kits containing the carrier molecule/chelating agent complex plus any reagents necessary to allow the chelation of the radioactive isotope to which the solution containing the radioactive isotope itself is simply added to get the labeled molecule ready for use.

Among the isotopes used in nuclear imaging, the Ga-68 is object of growing interest due to its high positronic yield (89%), its advantageous half-life (68 min.) and its availability through a generator, which makes it independent of the presence of a cyclotron. Moreover, due to its metallic nature, the Ga-68 can easily replace the isotopes used in therapy Y-90, In-111 and Lu-177, providing a diagnostic counterpart to all the molecules that, bonded to a suitable chelating agent, are used in the metabolic radiotherapy.

All of these aspects can give way to a new generation of radiopharmaceuticals in kits that could represent the PET version of the approach underlying the routine use of Tc-99 min SPECT.

However, on the other hand, although the Ga-68 is suitable for direct labeling and independent of the presence of a cyclotron, and therefore is a candidate as an isotope useful for the preparation of the kits as described above, there are still obstacles to the success of this type of approach. In addition to purely chemical aspects related to the labeling conditions, fears that the parent isotope Ge-68 may contaminate the radiopharmaceutical labeled with Ga-68 strongly hinders a labeling strategy based on the use of eluates containing Ga68 directly deriving from a Ge68/Ga68 generator, not pretreated and free from any type of purification. In fact, the Ge-68/Ga-68 generator from which the PET isotope Ga-68 is derived is based on the adsorption of the Ge-68 on a stationary phase and on the possibility of separating the daughter isotope Ga-68 generated from the decay of the parent isotope Ge-68 through the elution of the first one with a solution capable of selectively removing it from the stationary phase on which the second one is adsorbed. The risk associated with this operation is that traces of Ge-68 may be released into the solution of Ga-68 used in the labeling of radiopharmaceutical compounds.

All of this led the pharmaceutical authorities to set the maximum limit of 0.001% for the release of Ge-68 from the generator and to accept with reserve a labeling via a kit based on the use of the solution of Ga-68 as supplied by the generator without any purification or reduction of the potentially released content of Ge-68.

Moreover, even if a higher limit was set, the absence of higher accidental releases cannot be guaranteed.

Currently, the amount of Ge-68 released by the generator is minimized at the same time as the concentration and purification of the eluate prior to labeling in different ways known by the man skilled in the art of Ga-68 radiochemistry.

As is clear, therefore, the currently most important problem to solve is to ensure that the eluate deriving from a $^{68}$Ge/$^{68}$Ga generator is actually devoid of Ge-68; and multiple solutions have been tried to solve this problem.

One of these methods is based on the high distribution coefficient of Ga on a cation exchange resin so that it can be trapped and then released, only after the selective elimination of the parent isotope and other metal impurities with mixtures of acetone and HCl leading to high percentages of acetone in the eluent. A system for the isolation of purified Ga-68 based on this strategy was also patented (WO2006/056395).

However, this approach has some limitations related to the use of acetone as well as the need to remove the organic solvent and the possible formation of impurities, such as mesityl oxide.

An alternative approach uses the formation of the anionic chloride of the trivalent Ga GaCl4- in concentrated HCl (>4 N) and its subsequent adsorption on anion exchange columns, Once eluted from the generator, the solution of Ga-68 should be acidified by the addition of HCl and must be charged on an anion exchange cartridge on which the Ga-68 is retained and then eluted with small volumes of water. Under these conditions, the Ge-68 is not retained on the stationary phase. In a further version of this strategy (WO 2004/089517), the use of an anion exchanger with counterions HCO3- and a kit including the generator, a second anion exchange column and the HCl and water needed in the different steps of the elution are described.

The anionic strategy is also at the basis of an apparatus (US 2009/0001283) which uses a pump syringe and various valves to lead the separation of Ge-68 from the daughter isotope through the elution of Ga-68 from the generator column with citric add, the conversion of citrate gallium in tetrachloride gallium, its entrapment on a second column and the final elution with water or diluted HCl.

Another automated system was also described (US 2008/0035542) for the purification of radioisotopes and the formulation of radiopharmaceuticals that is also able to carry out the sequence of steps foreseen in the purification of Ga-68 on anion exchange resin.

More recently (WO 2011/033120), the complications related to the use of concentrated HCl were overcome by promoting the formation of gallium tetrachloride GaCl4- using concentrated solutions of chloride ions (preferably solutions of NaCl in HCl 0.1 M) and trapping the GaClx complex directly on an anion exchange resin. All of these methods claim to provide, in addition to the reduction of the volume of the eluate, also an effective purification from the parent isotope Ge-68.

Moreover, also the final purification on solid phase of the product labeled with Ga-68 (generally carried out on C18 cartridges) required by the current synthesis processes ensures a further reduction of Ge-68.

Therefore, the labeling methods with Ga-68 currently in use are based on multi-step processes comprising a prepurification of the eluate of the generator (anionic, cationic or by fractioning) and the purification of the final labeled product on C18 cartridges.

All of these steps are needed to improve the result of labeling with Ga-68 by concentrating the reaction volume and eliminating the unreacted Ga-68.

As a parallel result, they also produce a reduction of the Ge-68 potentially released by the generator.

It is clear that the availability of eluates containing Ga-68 in the absence of Ge-68, which therefore allow labeling a kit directly and with yields close to 100% without the need to reduce the volume of the eluate before labeling or to eliminate the unreacted Ga-68 at the end of the labeling would make the process steps described above unnecessary.

SUMMARY OF THE INVENTION

The present invention allows solving the above problem by completely reversing the logic used in the current labeling methods in which the Ga-68 is first trapped on specific columns to allow the removal of potential contaminants through subsequent washes, and then recovered in reduced volumes to be used in the labeling reaction.

DETAILED DESCRIPTION OF THE INVENTION

The process according to the invention allows in one step the trapping of the Ge-68 that needs to be eliminated from the eluate in output from the generator and thus directly use the solution of Ga-68 deriving from the generator for the reconstitution of the labeling kit without further treatment or steps.

The process according to the invention, by allowing the direct trapping of the Ge-68 while the eluate flows from the generator to the container containing the labeling kit as described above, allows widening the spread of Ga-68 similarly to what happens with the Tc-99m.

In order to achieve the above, the process according to the present invention uses a column comprising a suitable stationary phase which, placed at the generator output line, acts as a trap for the Ge-68.

In fact, it was surprisingly found that silica is capable of exerting the dual action of trapping the Ge-68 and letting the Ga68 freely pass simultaneously with the passage of the eluate of the generator without needing washing and elution steps, which prevents complicating or prolonging the labeling procedure, allowing an effective purification at the same time as the addition of the eluate to the kit.

It should be noted that, although silica is well known as stationary phase for chromatographic purifications, it has never been used for the trapping of Ge-68 in the radionuclidic purification of eluates from Ge-68/Ga-68 generators nor it could be expected to exercise the dual action as described above on the components of the eluate deriving from a $^{68}$Ge/$^{68}$Ga generator and on the other hand, other materials commonly used as stationary phase for chromatographic purification columns were not capable of carrying out the same action.

In particular, in order to be effective in the process according to the invention, the silica must have granulometry not higher than 250 microns, preferably less than 100 microns. Optimal results were obtained with silica having granulometry of less than 50 microns, preferably comprised between 20 e 10 microns.

This type of silica can therefore be used for the preparation of the chromatographic columns to be used in the process according to the invention directly connected to a $^{68}$Ge/$^{68}$Ga generator according to the standard preparation techniques used in the field.

In particular, according to the invention, disposable columns may be prepared in which the amount of silica is between 2 g and 200 mg. Said columns are placed at the output of the generator to purify the solution of Ga-68 from Ge-68.

By passing the radioactive solution eluted from a Ge-68/Ga-68 generator through the column thus prepared, only a negligible amount of Ga-68 remains retained in the column while almost all of the Ge-68 remains trapped, thus allowing an eluate to be obtained which fully meets the needs of purity required by the regulations for the labeling kits with Ga68.

It should be noted that the column according to the invention retains the Ge-68 present in the eluate as is, without the need to change the pH or the composition, so as to allow directly recovering a purified solution of Ga-68 avoiding intermediate dilution, concentration and/or transfer steps. The entrapment of Ge-68 by a simple passage on a dedicated cartridge does not complicate or prolong the labeling procedures, providing a radionuclidic purification along with the elution of the generator.

It should be noted that the use of such a cartridge offers the possibility to prepare a kit that allows the labeling with Ga-68 by the direct addition of the eluate deriving from the generator to the substrate to be labeled, without any other accessory operation.

Example 1

Purification of a Solution of Ga-68 in HCl 0.1 N 10 empty plastic columns provided with polyethylene partitions were charged with 650 mg of pharmaceutical grade silica with granulometry of 20-10 microns.

The cartridges thus obtained were used without any washing or pre-conditioning in 10 elution tests of a Ge-68/Ga-68 generator based on TiO2.

Each column was connected to the output of the generator and the solution of Ga-68 obtained by eluting the generator with 5 ml of HCl 0.1 N was directly collected in a bottle.

The activity of Ga-68 in the eluate and in the cartridge was measured immediately while the samples were left to decay for 2 days before measuring the content of Ge-68 by HP-Ge gamma spectrometry.

In the 10 tests, the average activity of Ga-68 retained by the columns was 3% while the activity of Ge-68 retained was on average 90% of the total amount released by the generator.

Example 2

Purification of a Solution of Ga-68 in HCl 0.05 N 10 empty plastic columns provided with polyethylene partitions were charged with 650 mg of pharmaceutical grade silica with granulometry of 20-10 microns.

The resulting cartridges were used without any washing or pre-conditioning in 10 elution tests of a Ge-68/Ga-68 generator based on organic resin.

Each column was connected to the output of the generator and the solution of Ga-68 obtained by eluting the generator with 5 ml of HCl 0.05 N was directly collected in a bottle.

The activity of Ga-68 in the eluate and in the cartridge was measured immediately while the samples were left to decay for 2 days before measuring the content of Ge-68 by HP-Ge gamma spectrometry.

In the 10 tests, the average activity of Ga-68 retained by the columns was 4% while the activity of Ge-68 retained was on average 95% of the total amount released by the generator.

The invention claimed is:

1. Process for the preparation of a radiopharmaceutical containing $^{68}$Ga wherein a solution of eluates from $^{68}$Ge/$^{68}$Ga generators is passed through a column for chromatography purification comprising a stationary phase of silica having a granulometry less than 100 microns and thereafter the solution collected from the column is directly poured in a container containing a labeling kit, the labeling kit comprising a substrate to be labeled with $^{68}$Ga, wherein the substrate subsequently labeled with $^{68}$Ga is the radiopharmaceutical.

2. A radiopharmaceutical kit comprising the radioactive isotope $^{68}$Ga produced through the process according to claim 1.

* * * * *